United States Patent [19]
Kwak et al.

[11] Patent Number: 6,084,152
[45] Date of Patent: Jul. 4, 2000

[54] METHOD FOR PRODUCING TRANSGENIC CUCUMBER THAT PRODUCES HIGH LEVELS OF SUPEROXIDE DISMUTASE

[75] Inventors: Sang Soo Kwak; Jae-Whune Kim; Haeng-Soon Lee; Suk Yoon Kwon, all of Taejon-si, Rep. of Korea

[73] Assignee: Korea Institute of Science and Technology, Rep. of Korea

[21] Appl. No.: 09/291,562

[22] Filed: Apr. 14, 1999

[30] Foreign Application Priority Data

Apr. 14, 1998 [KR] Rep. of Korea ............ 98-13205
Aug. 21, 1998 [KR] Rep. of Korea ............ 98-33947
Apr. 6, 1999 [KR] Rep. of Korea ............ 99-11848

[51] Int. Cl.[7] .................. C12N 5/04; C12N 15/29; C12N 15/82; C07H 21/04; A01H 5/00
[52] U.S. Cl. .................. 800/287; 800/278; 800/289; 800/294; 800/307; 800/309; 514/783; 435/430.1; 435/431; 435/469; 435/252.3; 435/320.1; 435/252.2; 536/23.2; 536/23.6; 536/23.1
[58] Field of Search .................. 800/278, 287, 800/289, 294, 307, 309, 317.1, 317.4, 313; 514/783; 435/430.1, 431, 252.3, 469, 320.1, 252.2; 536/23.2, 23.6, 23.1

[56] References Cited

U.S. PATENT DOCUMENTS

| | | | |
|---|---|---|---|
| 4,943,674 | 7/1990 | Houck et al. | 800/205 |
| 5,422,259 | 6/1995 | De Both et al. | 435/172.3 |
| 5,538,878 | 7/1996 | Thomas et al. | 435/172.3 |
| 5,616,323 | 4/1997 | Ginoux et al. | 424/195.1 |

FOREIGN PATENT DOCUMENTS 359617  3/1990  European Pat. Off. .

OTHER PUBLICATIONS

Ohkawa et al. Proc. Natl. Acad. Sci. USA, vol. 86, pp. 1239–1243, Feb. 1989.

Randy D. Allen, "Dissection of Oxidative Stress Tolerance Using Transgenic Plants", *Plant Physiol.* vol. 107: 1049–1054 (1995).

*Primary Examiner*—David T. Fox
*Assistant Examiner*—Medina A. Ibrahim
*Attorney, Agent, or Firm*—Gates & Cooper

[57] ABSTRACT

The invention relates to a transgenic plant that produces high levels of superoxide dismutase (SOD) and to a method for producing the transgenic plant. The hypocotyl section of seedlings is co-cultured with Agrobacterium transformant and regenerated by adventitious shoot induction and by root induction, where the Agrobacterium transformant contains an expression vector that comprises the promoter of a fruit-dominant ascorbate oxidase gene, an SOD gene isolated from cassava, and an herbicide-resistant bar gene. The present invention also relates to a method for inducing adventitious shoot from hypocotyl sections in plant tissue culture, thus providing a method for the efficient production of transgenic plants maintaining higher SOD activity in fruits. Therefore, the SOD transgenic cucumber of the present invention can be used for cosmetics, additives in functional foods, and medicines as well as having tolerance to herbicides and environmental stresses.

17 Claims, 8 Drawing Sheets

(5 of 8 Drawing Sheet(s) Filed in Color)

SEQUENCE LISTING

```
<160> NUMBER OF SEQ ID NOS: 10

<210> SEQ ID NO 1
<211> LENGTH: 801
<212> TYPE: DNA
<213> ORGANISM: Manihot esculenta
<220> FEATURE:
<221> NAME/KEY: CDS
```

-continued

```
<222> LOCATION: (55)...(510)
<221> NAME/KEY: polyA_site
<222> LOCATION: (781)...(801)
<221> NAME/KEY: polyA_signal
<222> LOCATION: (611)...(616)

<400> SEQUENCE: 1
tctcgatctt ctctgtctaa gctctaaagg ggtgctctga gatcacgtaa aaca atg        57
                                                           Met
                                                             1 gtg aag gct gaa gct gtt ctt acc agt agt gag ggg gtt agc gga aca       105
Val Lys Ala Glu Ala Val Leu Thr Ser Ser Glu Gly Val Ser Gly Thr
        5                  10                  15 atc ttc ttt acc caa gaa gga gat ggt cct acc act gta act gga aac       153
Ile Phe Phe Thr Gln Glu Gly Asp Gly Pro Thr Thr Val Thr Gly Asn
             20                  25                  30 att tcc ggc ctt aag cca ggg ctt cat ggg ttc cac gtc cat gcc ctt       201
Ile Ser Gly Leu Lys Pro Gly Leu His Gly Phe His Val His Ala Leu
         35                  40                  45 gga gac aca aca aac ggt tgc atg tca act ggg cca cac ttt aac cct       249
Gly Asp Thr Thr Asn Gly Cys Met Ser Thr Gly Pro His Phe Asn Pro
 50                  55                  60                  65 tct ggc aaa gat cat ggt gcc cct gag gat gag att cgt cat gct ggt       297
Ser Gly Lys Asp His Gly Ala Pro Glu Asp Glu Ile Arg His Ala Gly
                 70                  75                  80 gat ctg gga aat gtc act gct ggt gat gat ggc act gct agt ttc aca       345
Asp Leu Gly Asn Val Thr Ala Gly Asp Asp Gly Thr Ala Ser Phe Thr
             85                  90                  95 att att gac aag cat att cct ctt tct ggt caa aat tca atc ata gga       393
Ile Ile Asp Lys His Ile Pro Leu Ser Gly Gln Asn Ser Ile Ile Gly
        100                 105                 110 agg gca gtt gtt gtt cat gca gat cct gat gat ctt ggc agg gga gga       441
Arg Ala Val Val Val His Ala Asp Pro Asp Asp Leu Gly Arg Gly Gly
    115                 120                 125 cat gaa ctc agt aaa acc acc gga aat gct ggt ggc aga gta gca tgc       489
His Glu Leu Ser Lys Thr Thr Gly Asn Ala Gly Gly Arg Val Ala Cys
130                 135                 140                 145 ggt att att ggt ttg cga gga tagagtgctt ctccagagat caataacaag          540
Gly Ile Ile Gly Leu Arg Gly
                150 acaaagacag ctgaaacatg cacagccgga caacctttag aagaacgtta ggagaccatt     600 aactcatttg aataaaagaa agaataatac tgtagttttg gctggtttgg tcttgtgatc     660 tcaagatggt gtatgctttg tatggtttcg tgaagtttat tgaactttga acttttcga     720 atggtagggc ttgctctttg tctggtccaa attcaggccg tggatgtttt atactgcttt    780 aaaaaaaaaa aaaaaaaaa a                                                801

<210> SEQ ID NO 2
<211> LENGTH: 152
<212> TYPE: PRT
<213> ORGANISM: Manihot esculenta

<400> SEQUENCE: 2

Met Val Lys Ala Glu Ala Val Leu Thr Ser Ser Glu Gly Val Ser Gly
  1               5                  10                  15

Thr Ile Phe Phe Thr Gln Glu Gly Asp Gly Pro Thr Thr Val Thr Gly
             20                  25                  30

Asn Ile Ser Gly Leu Lys Pro Gly Leu His Gly Phe His Val His Ala
         35                  40                  45
```

-continued

```
Leu Gly Asp Thr Thr Asn Gly Cys Met Ser Thr Gly Pro His Phe Asn
 50                  55                  60

Pro Ser Gly Lys Asp His Gly Ala Pro Glu Asp Glu Ile Arg His Ala
 65                  70                  75                  80

Gly Asp Leu Gly Asn Val Thr Ala Gly Asp Gly Thr Ala Ser Phe
                 85                  90                  95

Thr Ile Ile Asp Lys His Ile Pro Leu Ser Gly Gln Asn Ser Ile Ile
                100                 105                 110

Gly Arg Ala Val Val His Ala Asp Pro Asp Leu Gly Arg Gly
            115                 120                 125

Gly His Glu Leu Ser Lys Thr Thr Gly Asn Ala Gly Arg Val Ala
    130                 135                 140

Cys Gly Ile Ile Gly Leu Arg Gly
145                 150
```

<210> SEQ ID NO 3
<211> LENGTH: 20
<212> TYPE: DNA
<213> ORGANISM: Other nucleic acid (synthetic oligonucleotide)
<220> FEATURE:
<221> NAME/KEY: misc_feature
<222> LOCATION: (1)...(20)
<223> OTHER INFORMATION: n = A,T,C or G

<400> SEQUENCE: 3
cttggncttc atggnttcca                                              20

<210> SEQ ID NO 4
<211> LENGTH: 20
<212> TYPE: DNA
<213> ORGANISM: Other nucleic acid (synthetic oligonucleotide)
<220> FEATURE:
<221> NAME/KEY: misc_feature
<222> LOCATION: (1)...(20)
<223> OTHER INFORMATION: n = A,T,C or G

<400> SEQUENCE: 4
ctnccaccag catttccagt                                              20

<210> SEQ ID NO 5
<211> LENGTH: 32
<212> TYPE: DNA
<213> ORGANISM: Other nucleic acid (synthetic oligonucleotide)

<400> SEQUENCE: 5
gcgcaagctt ctaaatattc tcttttaatt tg                                32

<210> SEQ ID NO 6
<211> LENGTH: 24
<212> TYPE: DNA
<213> ORGANISM: Other nucleic acid (synthetic oligonucleotide)

<400> SEQUENCE: 6
gcgcgaattc ttcgaagggt tgag                                         24

<210> SEQ ID NO 7
<211> LENGTH: 25
<212> TYPE: DNA
<213> ORGANISM: Other nucleic acid (synthetic oligonucleotide)

<400> SEQUENCE: 7
gcgcctgcag tctcgatctt ctctg                                        25

-continued

```
<210> SEQ ID NO 8
<211> LENGTH: 25
<212> TYPE: DNA
<213> ORGANISM: Other nucleic acid (synthetic oligonucleotide)

<400> SEQUENCE: 8
gcgcggatcc aacatccacg gcctg                                    25

<210> SEQ ID NO 9
<211> LENGTH: 20
<212> TYPE: DNA
<213> ORGANISM: Other nucleic acid (synthetic oligonucleotide)

<400> SEQUENCE: 9
ggtctgcacc atcgtcaacc                                          20

<210> SEQ ID NO 10
<211> LENGTH: 20
<212> TYPE: DNA
<213> ORGANISM: Other nucleic acid (synthetic oligonucleotide)

<400> SEQUENCE: 10
tcagatctcg gtgacgggca                                          20
```

METHOD FOR PRODUCING TRANSGENIC CUCUMBER THAT PRODUCES HIGH LEVELS OF SUPEROXIDE DISMUTASE

This application claims the benefit of Korean patent application serial numbers 98-13205, filed Apr. 14, 1998; 98-33947, filed Aug. 21, 1998; and 99-11848, filed Apr. 6, 1999, the entire contents of which are hereby incorporated by reference into this application.

Throughout this application various publications are referenced. The disclosures of these publications in their entireties are hereby incorporated by reference into this application in order to more fully describe the state of the art to which this invention pertains.

FIELD OF THE INVENTION

The present invention relates to a transgenic plant producing high levels of superoxide dismutase (hereinafter, referred to as SOD) and methods for producing transgenic plants. More particularly, the transgenic plant of the present invention can be produced by co-culturing the hypocotyl section of a seedling with a transformant and by regenerating the infected hypocotyl section using a novel method for inducing adventitious shoot, where the transformant contains an expression vector for transforming plants. The expression vector comprises a fruit-dominant promoter of cucumber ascorbate oxidase gene (hereinafter referred to as ASO promoter), an SOD gene isolated from cassava, and a herbicide-resistant gene. The transgenic plant of the present invention is efficiently produced, maintaining higher SOD activity in fruits, and can be used for materials of cosmetics, additives in foods, and medicines as well as having tolerance to herbicides and environmental stresses.

BACKGROUND

In response to environmental stresses as well as biological stresses induced by pathogens, insects, viruses and so on, most living organisms, including plants, convert oxygen to reactive oxygen species such as superoxide anion radical, hydrogen peroxide, and hydroxyl radical. Superoxide anion radical ($.O_2$) is generated from the reaction of molecular oxygen with a free electron. In the presence of iron, hydrogen peroxide is converted to hydroxyl radical ($.OH$), the most toxic reactive oxygen species. These reactive oxygen species are so reactive that they cause serious physiological damage to organisms.

To eliminate reactive oxygen species, living organisms have various antioxidant systems, which include macromolecular antioxidant enzymes such as SODs, peroxidases, catalases and so on, and other antioxidant molecules such as vitamin C, vitamin E, glutathione and so on. SODs are ubiquitous enzymes converting superoxide anion radical to hydrogen peroxide. To prevent the formation of hydroxyl radical, either peroxidases or calatases scavenge hydrogen peroxide, converting it to water. Thus, SODs play important roles in the antioxidant system and defense mechanism of living organisms, scavenging superoxide anion radical and preventing the formation of hydroxyl radical.

Since SODs are important factors improving tolerance in organisms to environmental stresses, there is a desire to introduce SOD as an ingredient of medicines, foods, cosmetics, and the like. In addition, transgenic plants into which SOD gene is transferred have been produced in order to develop plants tolerant to various environmental stresses, such as ozone, low temperature, herbicides and so on (*Plant Physiol.*, 10, 1049–1054, 1995; U.S. Pat. No. 5,538,878).

It has been reported that SOD is effective on arthritis, rheumatism, ischemic heart disease, radiation hazard and the like. It has been recently revealed that, when applied to UV-irradiated skin, SOD causes recovery of the damaged skin (*Experimental Dermatology*, 6, 116–121, 1997). These advances have led to the development of medicines which comprise SOD as an active ingredient by pharmaceutical companies in America, Japan, and so on. Additionally, SOD-containing cosmetics to prevent aging of skin have been developed and commercialized in Korea (SOD and active oxygen modulators: pharmacology and clinical trials, NIHON-IGAKUKAN, 1989).

However, because purified SOD loses its activity quickly, there has been an obstacle to the production of medicines or cosmetics in which SOD activity is maintained.

SUMMARY OF THE INVENTION

To solve this problem, and to overcome other limitations of the prior art, the inventors of the present invention have developed a plant producing high levels of SOD, and have developed a plant bioreactor system by which SOD is overexpressed in edible plant tissue.

The invention provides a CuZn SOD gene, the first SOD gene isolated from cassava cultured cells, and variants thereof. In one embodiment, the SOD gene comprises the nucleotide sequence shown in SEQ ID NO:1 or a variant thereof.

The invention provides an expression vector comprising a cucumber fruit-dominant promoter, a superoxide dismutase (SOD) gene, and a selectable marker gene. In one embodiment, the cucumber fruit-dominant promoter is an ascorbate oxidase (ASO) promoter. In one embodiment, the expression vector has a restriction map as shown in FIG. 1 and designated ASOp+mSOD1/pGPTV-Bar. In one embodiment, the selectable marker gene comprises an herbicide-resistant gene. The herbicide-resistant gene preferably comprises a bar gene.

The invention additionally provides a transformant comprising the above expression vector. Preferably, the transformant is an Agrobacterium, such as *Agrobacterium tumefaciens*. Most preferably the transformant is *Agrobacterium tumefaciens* LBA 4404 having KCTC Accession No. 0585BP The invention provides a method for producing a transgenic plant. The method comprises co-culturing a transformant of the invention with plant tissue, and regenerating the transformed tissue into a transgenic plant. Examples of plant tissue that can be used include, but are not limited to, a woody plant, a vegetable, a legume, a monocotyledon and a member of the Cucurbitaceae family. Preferably, the plant tissue is selected from the group consisting of cucumber (*Cucumis sativus* L.), tomato (*Lycopersicon esculentum*), Chinese matrimony vine (*Lycium chinense* Mill), red pepper (*Capsicum annuum* L.), melon (*Cucumis melo* L.), bean (*Phaseolus vulgaris* L.), and spring onion (*Allium fistulosum* L.).

The invention provides an additional method for producing a transgenic plant. The method comprises excising a portion of hypocotyl of a germinated seedling. Preferably, the upper hypocotyl is excised to eliminate the root portion of the seedling. More preferably, the excised hypocotyl is approximately 6 mm in length, and most preferably, approximately 2 to approximately 3 mm in length. In one embodiment, the hypocotyl portion is excised at about 3 to about 5 days after germination. Preferably, the excising is performed when the germinated seedling has one intact cotyledon or two half-cotyledons.

The method further comprises infecting the excised hypocotyl portion with a transformant, culturing the infected hypocotyl portion in medium under conditions sufficient for adventitious shoot induction, and regenerating the infected hypocotyl portion into a transgenic plant. In one embodiment, the adventitious shoot is induced from the infected hypocotyl portion on selective medium. In a preferred embodiment, the induced adventitious shoot is rooted in medium under conditions sufficient for root induction, and the rooted plantlet is acclimatized to soil.

The invention additionally provides a transgenic plant produced by the a method of the invention and derivatives of these transgenic plants. Also provided is a composition comprising a transgenic plant of the invention or a derivative thereof, and a suitable carrier. Preferably the composition is a cosmetic composition, a nutriceutical composition or a pharmaceutical composition. The invention also provides a method of administering SOD to a subject comprising administering a composition of the invention to the subject. Preferably, the administration is topical or oral.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 2 depicts the processes in which the regenerated plants are prepared, where:

2C+H represents the induction frequency from the hypocotyl section of seedlings with two intact cotyledons, 1C+H represents the induction frequency from the hypocotyl section of seedlings with one intact cotyledon, (½C+½C)+H represents the induction frequency from the hypocotyl section of seedlings with two half-cotyledons, and ½C represents the induction frequency from cotyledon segments.

Figure 4:
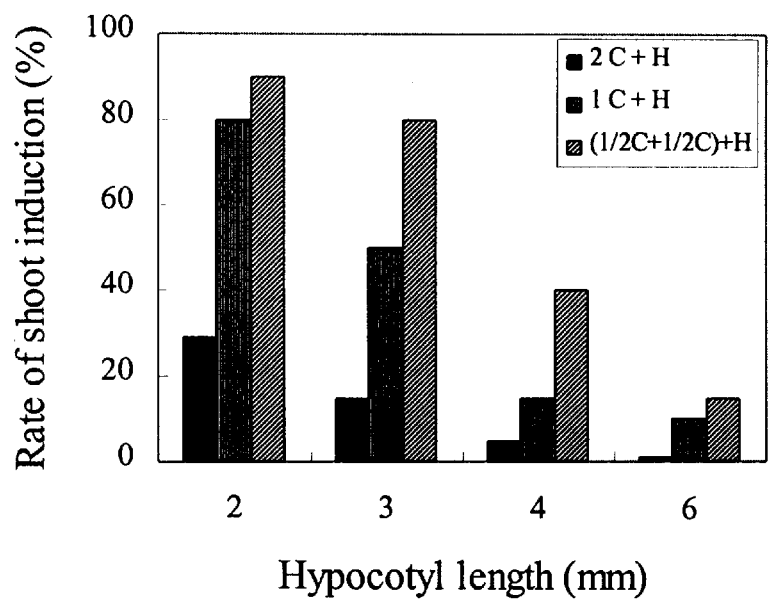

FIG. 4 depicts the relationship between the hypocotyl length of 5 DAG (day-after-germination) seedlings and the frequency of adventitious shoot induction from the hypocotyl section, where:

2C+H represents the induction frequency from the hypocotyl section of seedlings with two intact cotyledons, 1C+H represents the induction frequency from the hypocotyl section of seedlings with one intact cotyledon, and (½C+½C)+H represents the induction frequency from the hypocotyl section of seedlings with two half-cotyledons.

Figure 5A:
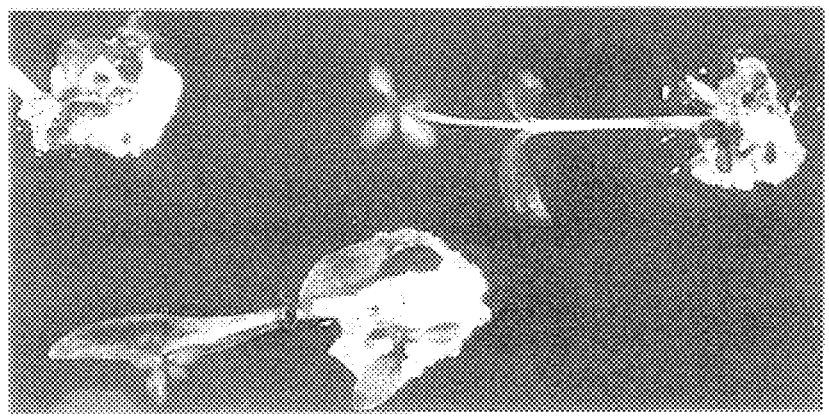
Figure 5B:
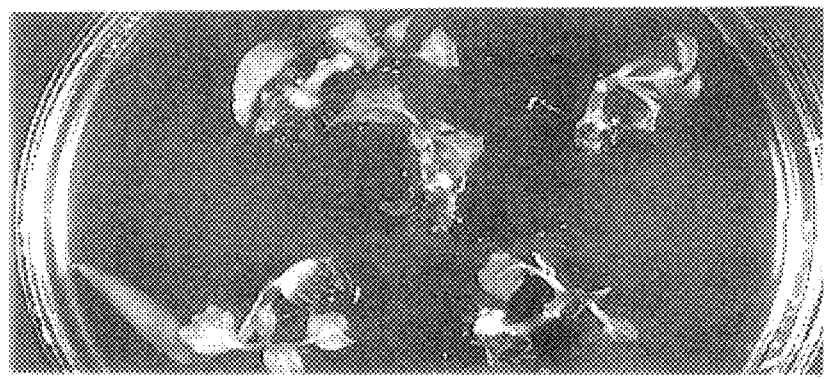
Figure 5C:
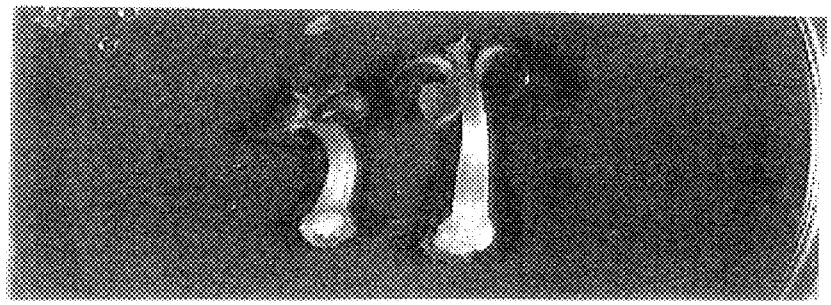
Figure 5D:
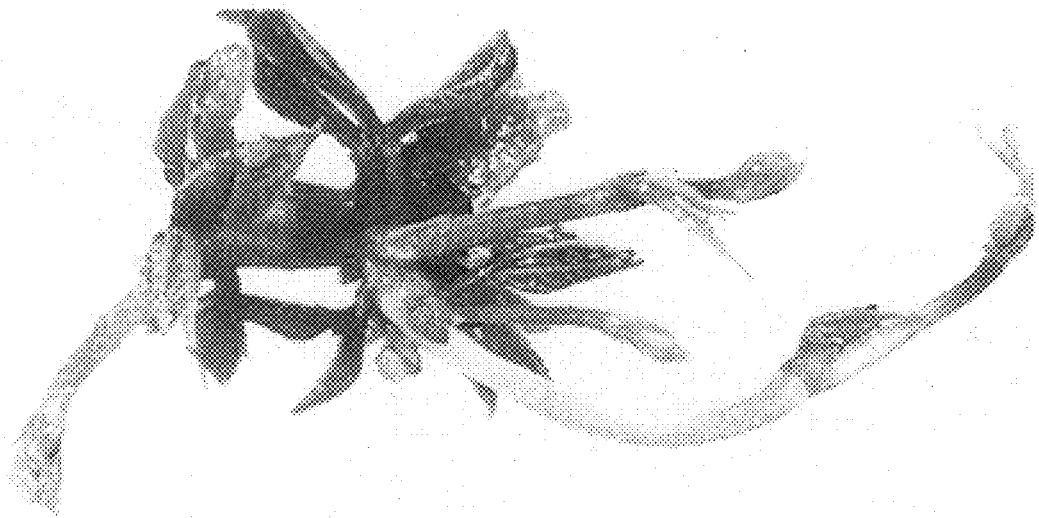
Figure 5E:
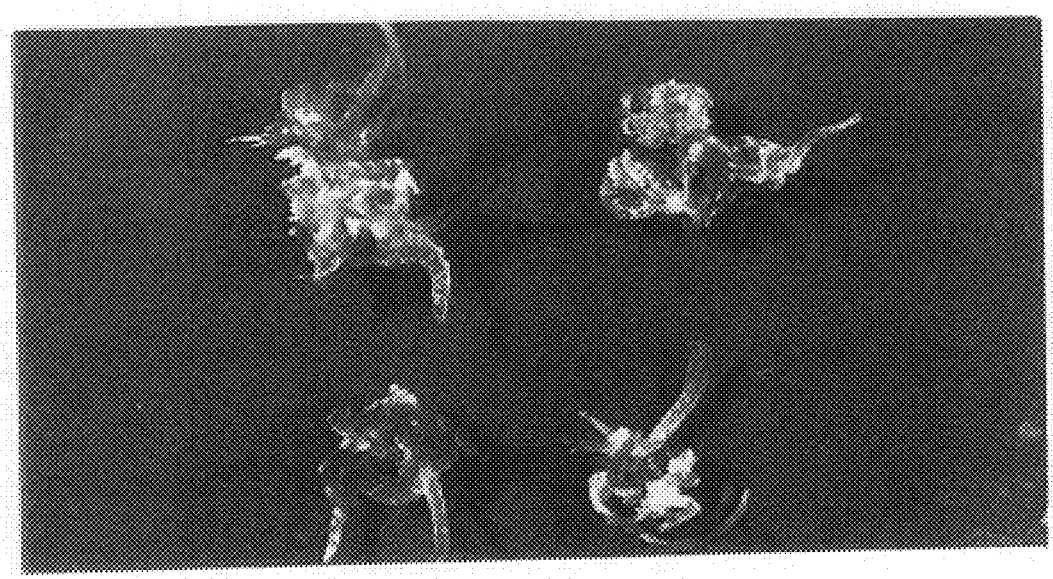

FIG. 5 depicts the adventitious shoots induced efficiently from the hypocotyl section of various seedlings such as Chinese matrimony vine, red pepper, melon, bean, and spring onion, where:

FIG. 5a represents the adventitious shoots induced efficiently from the hypocotyl section of Chinese matrimony vine seedlings, FIG. 5b represents the adventitious shoots induced efficiently from the hypocotyl section of red pepper seedlings, FIG. 5c represents the adventitious shoots induced efficiently from the hypocotyl section of melon seedlings, FIG. 5d represents the adventitious shoots induced efficiently from the hypocotyl section of bean seedlings, and FIG. 5e represents the adventitious shoots induced efficiently from the hypocotyl section of spring onion seedlings.

Figure 6A:
Figure 6B:
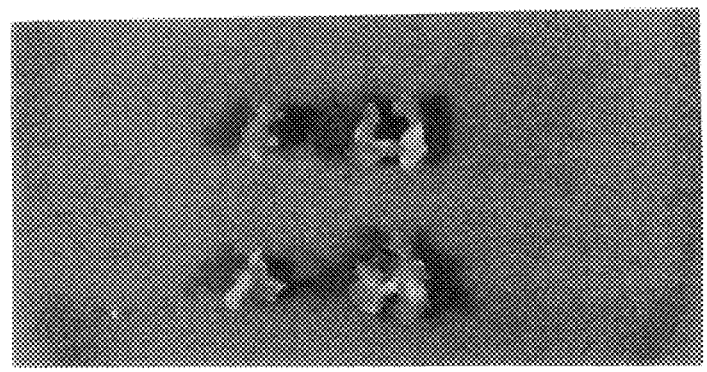
Figure 6C:

FIG. 6 depicts the processes in which SOD transgenic cucumbers are prepared through the adventitious shoots induced by co-culturing the hypocotyl section with Agrobacterium transformant, where:

FIG. 6a represents transformed adventitious shoots on hypocotyl section,

FIG. 6b represents the rooted adventitious shoots, which is excised from the seedlings, and FIG. 6c represents the regenerated transgenic cucumbers in pots.

Figure 7:
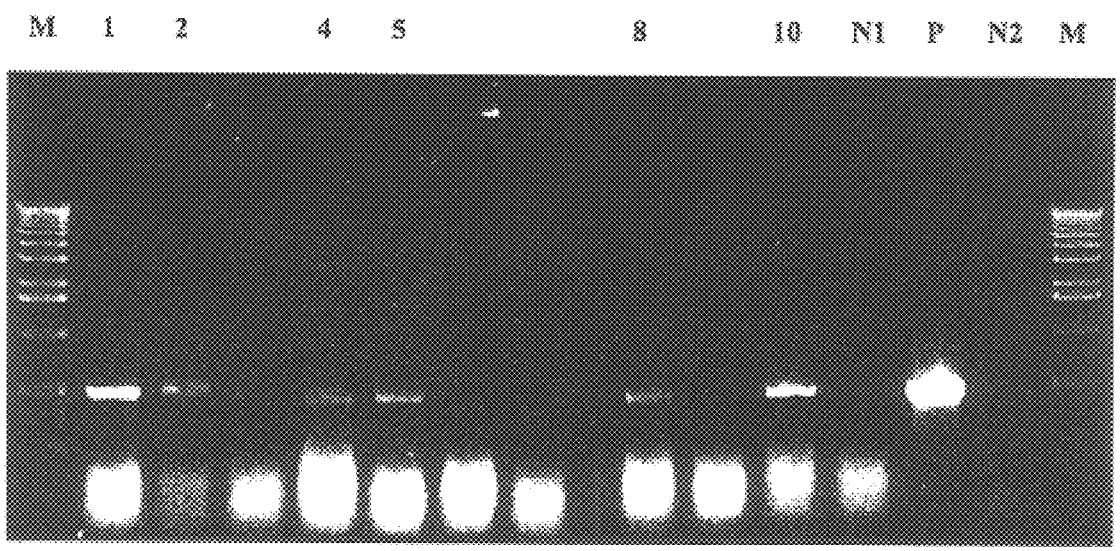

FIG. 7 depicts the introduction of SOD gene into the genomes of transgenic cucumbers, by polymerase chain reaction (hereinafter, referred to as PCR) and subsequent DNA gel electrophoresis, where:

Lane 1, 2, 4, 5, 8, 10 represents PCR products from transformants,

N1 represents PCR products from non-transformants,

N2 represents negative control of PCR, in which no template is added,

M represents DNA size marker, and represents positive control of PCR, in which vector ASOp+mSOD1/pGPTV-Bar is used as template.

DETAILED DESCRIPTION OF PREFERRED EMBODIMENTS

Plant bioreactor systems overexpressing a specific gene in plant tissue have been occasionally reported. For example, an edible vaccine was produced from transgenic banana into which a vaccine gene was introduced (*Bio/Technology*, 13, 379–392, 1995). However, an SOD gene has not been overexpressed in edible plants.

Cucumber (*Cucumis sativus* L.) is a high value-added food, and massage packs using cucumber are utilized broadly, because of its various functions such as the supply of nutrients, the removal of wastes and keratin, suppressive effect on inflammation, whitening, moisturizing, and the like (Techniques for cultivation of cucumber, Kurye Cucumber Experimental Station in Korea, 1997). Although cucumber has such advantages, SOD content (units/mg protein) in cucumber fruits is much lower than those in other tissues.

Thus, if SOD activity is elevated through transfer of SOD gene into cucumber fruits, the resulting transgenic cucumber will synergistically acquire a preferable trait of higher SOD activity, in addition to known benefits of cucumber. The inventors of the present invention have developed a plant bioreactor system through the production of transgenic plants overexpressing SOD. In a preferred embodiment, an SOD gene in the form of an expression vector for transforming plants is introduced into Agrobacterium, and plant tissue is co-cultured with the Agrobacterium transformant, then regenerated to adult plants overexpressing SOD gene.

In order to produce the transgenic plants efficiently, plant tissues into which foreign genes are introduced should be regenerated. Thus, the inventors of the present invention have established a novel and more efficient method for inducing adventitious shoot from the cultured hypocotyl section, repeatedly and regardless of the species or cultivar of seed plants. The present invention is performed by the production of the SOD transgenic plants, which is regenerated through the novel method for inducing adventitious shoot.

The present invention provides a transgenic plant that produces high levels of SOD.

The present invention provides a method for producing a transgenic plant, wherein SOD gene in the form of an expression vector for transforming plants is introduced into Agrobacterium, and then plant tissue is co-cultured with the resulting Agrobacterium transformant.

The present invention provides an expression vector for transforming plants with SOD gene.

The preferred expression vector for transforming plants in accordance with the present invention is ASOp+mSOD1/pGPTV-Bar, which comprises CuZn SOD cDNA (mSOD1) isolated from the cultured cells of cassava, a herbicide (Basta)-resistant bar gene as a selectable marker, and ASO promoter.

The present invention provides an Agrobacterium transformant, into which the expression vector ASOp+mSOD1/pGPTV-Bar is introduced.

The preferred Agrobacterium transformant of the present invention is *Agrobacterium tumefaciens* LBA 4404 (ASOp+mSOD1/pGPTV-Bar).

The present invention provides a method for producing regenerated plants, comprising following steps:
 a) the excision of the upper hypocotyls of germinated seedlings,
 b) the induction of adventitious shoot from hypocotyl section,
 c) the induction of root from the induced adventitious shoot, and
 d) the acclimatization of resulting plantlets to soil.

The present invention provides a method for producing regenerated transgenic plants, wherein a useful gene is transferred into an excised hypocotyl section, and then adventitious shoot is induced from there.

In addition, the present invention provides uses of the SOD transgenic plant for materials of cosmetics including massage pack, for additives in functional foods, and for Basta-resistant plant.

Definitions

All scientific and technical terms used in this application have meanings commonly used in the art unless otherwise specified. As used in this application, the following words or phrases have the meanings specified.

As used herein, "vector" means a construct which is capable of delivering one or more gene(s) or sequence(s) of interest in a host cell. In a preferred embodiment, the host cell is a bacterial transformant. Most preferably, the transformant is *Agrobacterium tumefaciens*.

As used herein, "promoter" means a nucleic acid sequence that directs transcription of a nucleic acid. A promoter can be a constitutive or an inducible promoter, or an enhancer. The promoter is operably linked to the nucleic acid sequence to be transcribed.

As used herein, "variant" of a nucleotide sequence means a nucleotide molecule encoding an SOD having one or more amino acid substitutions or deletions in the amino acid sequence shown in SEQ ID NO: 2, yet retaining SOD activity.

As used herein, "derivative" means a portion or portions of the plant. In a preferred embodiment, the portion or portions of the plant have been further processed in a manner that enhances SOD activity.

As used in the appended claims, "a" refers to at least one, and can include a plurality.

As used herein, "suitable carrier" includes any material which, when combined with an active ingredient of a composition, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents.

Compositions comprising such carriers are formulated by well known conventional methods (see, for example, Remington's Pharmaceutical Sciences, Chapter 43, 14th Ed., Mack Publishing Col, Easton Pa. 18042, USA). Compositions of the invention include cosmetic, nutriceutical and pharmaceutical compositions. A cosmetic composition is suitable for use in methods that enhance the appearance of a subject. A nutriceutical composition is suitable for consumption by a subject and has nutritional value, such as foods, nutiritional supplements and other edible products. A pharmaceutical composition is suitable for therapeutic use.

Hereinafter, the present invention is described in detail.

To produce the transgenic plant which produces SOD dominantly in fruits, the present invention exploits an expression vector for transforming plants, which preferably comprises ASO promoter, mSOD1 gene, and bar gene. The vector is introduced into a transformant, such as Agrobacterium to produce a transformant, with which plant tissue is co-cultured. In the co-culture process, organ culture is exploited to induce adventitious shoot from the hypocotyl section of germinated seedlings and to induce root from the adventitious shoot, leading to regeneration of plants.

The regeneration method using organ culture, comprises:
 a) the germination of sterilized seeds on MS medium without plant growth regulators,
 b) the excision of hypocotyl of germinated seedlings,
 c) the induction of adventitious shoots from hypocotyl section,
 d) the induction of roots from the adventitious shoot, and
 e) the acclimatization of the plantlets to soil.

In the process of adventitious shoot induction, the hypocotyl section is cultured under lights, which occasionally leads to poor induction from the hypocotyl section of some plant species. In this case, induction frequency can be elevated, by culturing the plants under darkness for a specified period and then transferring them to light.

In addition, the preferable age of seedlings is 3–5 DAG (days after germination), the preferable hypocotyl length in the excision process is 2–3 mm, and the preferable seedlings have either one intact cotyledon or two half-cotyledons, although these preferences are variable according to plant species.

As shown above, the present invention provides a method for producing normal, regenerated plants by inducing adventitious shoot from the hypocotyl section. By the method, adventitious shoots are abundantly obtained from the hypocotyl section of various seed plants, examples of which include cucumber (*Cucumis sativus* L.), Chinese matrimony vine (*Lycium chinense* Mill), red pepper (*Capsicum annuum* L.), melon (*Cucumis melo* L.), bean (*Phaseolus vulgaris* L.), and spring onion (*Allium fistulosum* L.). Therefore, the method for inducing adventitious shoot can be effectively applied to plant regeneration, which is an essential process in the propagation of useful plants and the development of transgenic plants.

The novel method for inducing adventitious shoot provides relative advantages over methods in which only cotyledon segments are cultured. Such advantages include:

a) In the method using cotyledon segments, adventitious shoots may be originated from leaf primordia that are accidentally attached to the cotyledon segments. Employing the hypocotyl section as cultured material precludes this possibility.

b) If cotyledon segments are cultured from the seedlings of Cucurbitaceae family such as cucumber, the curled leaves with multiple layers are often induced, and the cultured explants do not develop the shoot apical meristem, or, if any develops, the explant often ceases to grow and shows collective dwarfism (*Plant Cell Report,* 9, 559–562, 1991; *J. Amer. Soc. Hort. Sci.,* 118, 151–157, 1993). On the contrary, the adventitious shoots induced from hypocotyl section in the present invention scarcely show the symptoms of either undifferentiation or collective dwarfism.

In addition, the method for inducing adventitious shoot is applicable to the efficient regeneration of transgenic plants, by transferring a useful foreign gene into the hypocotyl section and then inducing adventitious shoots from there. More particularly, the gene transfer is mediated by the infection of the hypocotyl section with *Agrobacterium tumefaciens* strain, which is transformed with a useful foreign gene.

In the present invention, the method for inducing adventitious shoot can be used to produce a plant overexpressing SOD gene. In detail, in order to produce the SOD transgenic plant, an expression vector for transforming plants with SOD gene is introduced into Agrobacterium, and the expression vector is transferred into plant tissue by co-culturing hypocotyl section with the Agrobacterium transformant.

The method for producing the transgenic plant, which is regenerated by the method for inducing adventitious shoot, comprises:

a) the construction of expression vector containing SOD gene, b) the production of Agrobacterium transformant with the vector in a), c) the germination of sterilized seeds, d) the excision of hypocotyl of germinated seedlings, e) the co-culture of hypocotyl section with the Agrobacterium transformant in b), f) the induction of adventitious shoots from the infected hypocotyl section on the selective medium, g) the induction of roots from the adventitious shoot, and h) the acclimatization of the plantlets to soil.

Agrobacterium used in b) process includes all the species of Agrobacterium, into which an expression vector for transforming plants can be introduced.

Plants used in the above processes include all the seed plants, and particularly edible plants including cucumber, tomato, and red pepper, are preferably used as these edible plants are applicable to healthful foods, cosmetics, medicines, and so on.

In order to produce the fruits or vegetables containing SOD abundantly and to use them as the materials for massage pack etc., the present invention exploits an expression vector for transforming plants. This expression vector comprises a promoter (ASO promoter) expressed dominantly in cucumber fruits (*Proc. Natl. Acad. Sci USA,* 86, 1239–1243, 1989; *Ann. N. Y. Acad. Sci.,* 721, 245–247, 1994), an SOD gene (mSOD1) isolated from cassava cultured cells, and a herbicide-resistant gene (bar).

Although SOD genes have been isolated from more than 30 plant species, a CuZn SOD gene (mSOD1, see SEQ ID NO. 1) which is isolated first from cassava (*Manihot esculenta*) cultured cells, is preferably used to construct the expression vector in the present invention.

Basta-resistant gene, bar, can be used as a selectable marker for the expression vector. Non-selective herbicide Basta is broadly used, since it has high herbicidal activity and causes less soil pollution than other herbicides. Phosphinothricin, a composite of Basta, is synthesized by *Streptomyces hygroscopicus,* and inhibits strongly the glutamine biosynthesis of plants. Application of phosphinothricin or Basta to plants elevates ammonia level in the plants, leading to browning and withering of the plants. bar encodes phosphinothricin acetyltransferase, an enzyme detoxifying phosphinothricin (*EMBO,* 6, 2519–2523, 1987). Therefore, bar has been frequently used to select transformed plants as well as to develop herbicide-resistant plants.

The preferred expression vector for transforming plants in accordance with the present invention is ASOp+mSOD1/pGPTV-Bar (see FIG. 1), which comprises mSOD1, bar, ASO promoter, and the like. This vector can be introduced into Agrobacterium, preferably *Agrobacterium tumefaciens.*

Deposited Strain

In the present invention, the strain *Agrobacterium tumefaciens* LBA 4404 is preferably used as an Agrobacterium strain, into which the expression vector is introduced. An Agrobacterium transformant of the present invention was designated as *Agrobacterium tumefaciens* LBA 4404 (ASOp+mSOD1/pGPTV-Bar), and deposited under the requirements of the Budapest Treaty with the Korean Collection for Type Cultures (KCTC) of the Korea Research Institute of Bioscience and Biotechnology (KRIBB), #52, Oun-dong, Yusong-ku, Taejon 305–333, Republic of Korea, on Mar. 6, 1999, identified as KCTC Accession No. 0585BP. All restrictions imposed by the depositor on the availability to the public of the deposited material will be irrevocably removed upon the granting of a patent in this U.S. application.

The fruits and vegetables of SOD transgenic plants, which are produced through the method of the present invention, show higher antioxidant activity, and thus can be used as materials of cosmetics, additives in functional foods, or medicines. Particularly, SOD transgenic cucumber and the like are useful for materials of cosmetics, for example, massage pack.

Additionally, since the SOD transgenic plants in the preferred embodiment of the present invention show tolerance to herbicide (Basta) as well as the higher antioxidant activity, they can be efficiently cultivated in stressful environments.

EXAMPLES

Practical and presently preferred embodiments of the present invention are illustrated in the following Examples. However, it will be appreciated that those skilled in the art, on consideration of this disclosure, may make modifications and improvements within the spirit and scope of the present invention.

Example 1

Figure 2A:
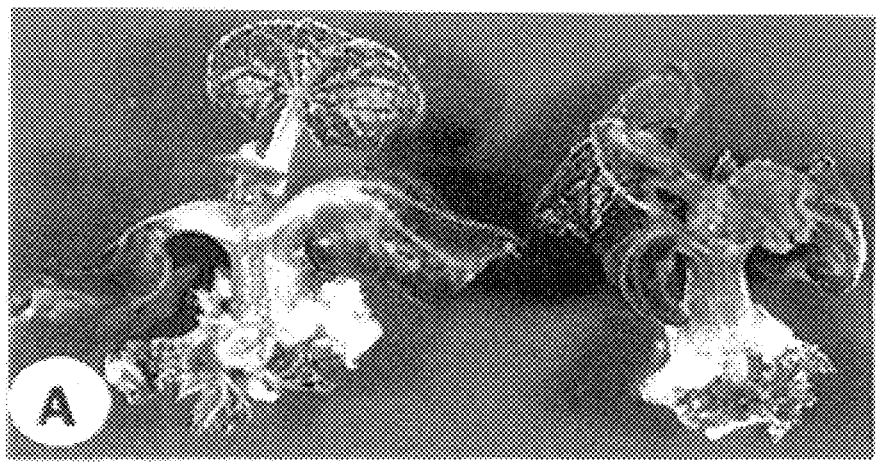
FIG. 2a represents the induction of adventitious shoots from the hypocotyl section.

Adventitious shoot induction and plant regeneration from hypocotyl sections of cucumber seedlings In order to regenerate plants through organogenesis, the seeds of five cucumber cultivars (Yoroomsamchuck, Eunsongbakdadagi, Bakbongdadagi, Chosengnakhap, Changhyongnakhap) were soaked in distilled water for 1 hour, sterilized in 75% ethanol for 1 minute and in 2% sodium hypochlorite for 15 minutes, and washed with sterile water three times. The sterilized seeds were germinated on MS media without growth regulators (Murashige and Skoog, Physiol. Plant 15, 473–497, 1962) at 25±1° C., with a photoperiod of 16 hours under fluorescent light (intensity: about 15 μmol m$^{-2}$·s$^{-1}$) and 8 hours under darkness. After various periods of germination, the upper region of the hypocotyl was excised to discard the lower part of the seedlings. The upper part of the excised seedlings was transferred to medium for adventitious shoot induction (MS medium supplemented with 2.0 mg/L zeatin), with the hypocotyl section of the seedlings contacting the medium. Seedlings on the medium were cultured, with a photoperiod of 16 hours under fluorescent light (intensity: about 15 μmol m$^{-2}$·s$^{-1}$) and 8 hours under darkness (see FIG. 2a). After 3 weeks, the adventitious shoots were induced from the hypocotyl sections of the seedlings, and the frequency of adventitious shoot induction was investigated (see below).

Figure 2B:
FIG. 2b represents the development of leaves from the adventitious shoots.
Figure 2C:
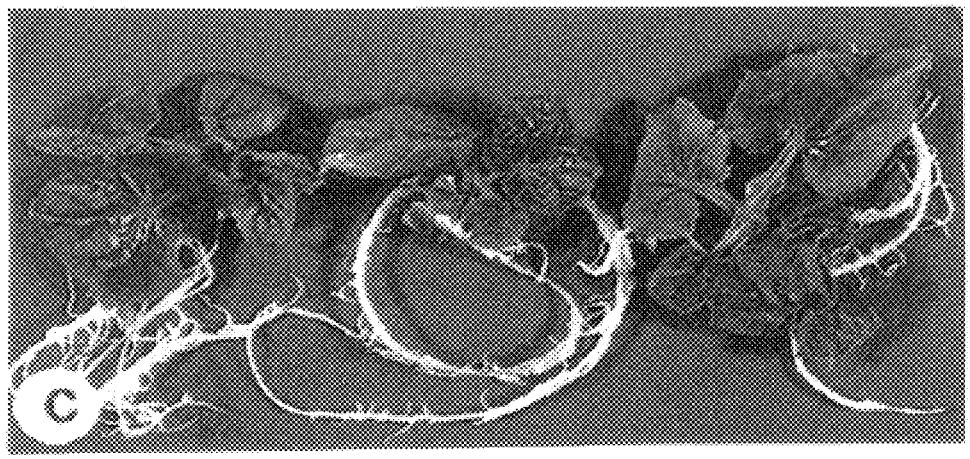
FIG. 2c represents the induction of roots.
Figure 2D:
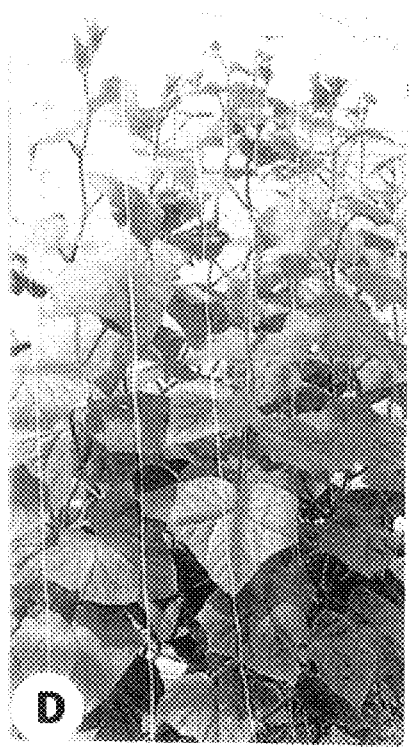
FIG. 2d represents the regenerated plants in pots.

The adventitious shoots developing 1 or 2 leaves (see FIG. 2b) were transferred to media for root induction, the MS media supplemented with 1.0 mg/L IAA (indole-3-acetic acid), and cultured for 2 weeks to be rooted easily (see FIG. 2c). Rooted plantlets with 2 or 3 leaves were transferred into pots, and acclimatized to soil under the condition of about 80% humidity. Regenerated plants could be grown to normal, fertile adult plants (see FIG. 2d).

To assess the frequencies of adventitious shoot induction from the hypocotyl section according to age (i.e. Days After Germination: hereinafter, referred to as DAG) of cucumber seedlings used, the upper hypocotyls of 3, 5, 7 or 9 DAG seedlings were excised to discard the lower part of the seedlings, leaving 2 mm-length hypocotyls. The excised seedlings were cultured on the media for adventitious shoot induction as described earlier. As a result, hypocotyl sections of 3 DAG seedlings efficiently produced adventitious shoots, whether the excised seedling had one or two cotyledons, or whether it had intact cotyledons or half-cotyledons (see FIG. 3). In the case of the seedlings with two cotyledons, 3 DAG seedlings produced adventitious shoots with high frequency (about 70%), while 5 DAG seedlings did not (below 30%) (see FIG. 3). Thus, the most preferable materials to culture are the 3~5 DAG seedlings which have either one cotyledon or two half-cotyledons, if one intends to induce adventitious shoot efficiently from hypocotyl sections of cucumber seedlings.

To investigate the relationship between the length of hypocotyl and the efficiency of adventitious shoot induction from the hypocotyl section, the hypocotyls of 5 DAG seedlings were excised to 2, 3, 4, or 6 mm-length, and cultured on MS media supplemented with 2.0 mg/L zeatin. As a result, the longer the hypocotyls were, the less adventitious shoots were induced from them (see FIG. 4), suggesting that cells in the upper hypocotyl are most competent for adventitious shoot formation. In the case of seedlings with two intact cotyledons, the efficiency of induction was remarkably reduced as the hypocotyl length increased. In addition, seedlings with 6 mm sections of the hypocotyl rooted on the media, which is a reasonable result because the presence of hypocotyl and two cotyledons may attenuate the effect of exogenous zeatin, and because the plant hormone auxin, synthesized in the shoot apical meristem, may induce root formation.

Again, the size of cotyledons has an effect on adventitious shoot induction: the section of 2 mm hypocotyl produced adventitious shoots with similar efficiency whether the excised seedling had one or two cotyledons or whether it had intact cotyledons or half-cotyledons, while the section of 3 mm hypocotyl with two half-cotyledons showed still higher efficiency than with two intact cotyledons (see FIG. 4). The results shown in FIG. 3 and FIG. 4 suggest that the number and the size of cotyledons have significant effects on adventitious shoot induction from the hypocotyl section.

Example 2
Comparative adventitious shoot induction from cucumber cotyledon segments In order to regenerate plants through organogenesis, the seeds of five cucumber cultivars (Yoroomsamchuck, Eunsongbakdadagi, Bakbongdadagi, Chosengnakhap, Changhyongnakhap) were soaked in distilled water for 1 hour, sterilized in 75% ethanol for 1 minute and in 2% sodium hypochlorite for 15 minutes, and washed with sterilized water three times. The sterilized seeds were germinated on MS media without growth regulators at 25±1° C., with a photoperiod of 16 hours under fluorescent light (intensity: about 15 μmol m$^{-2}$·s$^{-1}$) and 8 hours under darkness. The basal region (5 mm×5 mm) of the cotyledons of 5 or 7 DAG seedlings was cut and transferred onto medium for culture of cotyledon segments, which is an MS medium supplemented with 3% sucrose, 0.4% Phytagel, and cytokinin [1.0 or 2.0 mg/L zeatin, 1.0 mg/L 6-benzyladenine (BA), and 1.0 or 3.0 mg/L kinetin] with/without 0.1 or 0.2 mg/L indole-3-acetic acid (IAA). The medium was adjusted to pH 8.5, sterilized by autoclaving for 15 minutes at 121° C., 1.2 atm, on liquid cycle, and dispensed into 25 mL aliquots in Petri dishes (87 mm×15 mm). The Petri dishes containing five cotyledon segments were cultured at 25±1° C., with a photoperiod of 16 hours under fluorescent light (intensity: about 15 μmol m$^{-2}$·s$^{-1}$) and 8 hours under darkness. The cotyledon segments were grown for 4 weeks, and the investigation for the adventitious shoot formation was carried out.

TABLE 1

The adventitious shoot formation in the cucumber cotyledon segments which were cultured for 4 weeks in various compositions of plant hormones

| Contents in MS media (mg/L) | | | | No. of cotyledon segments used | No. of adventitious shoots induced | Frequency of adventitious shoot induction (%) |
| --- | --- | --- | --- | --- | --- | --- |
| BA | Kinetin | Zeatin | IAA | | | |
| 1.0 | | | | 315 | 4 | 1.3 |
| 1.0 | | | 0.1 | 720 | 32 | 4.4 |
| | 1.0 | | | 210 | 0 | 0 |
| | 1.0 | | 0.1 | 345 | 7 | 2.0 |
| | | 1.0 | | 324 | 11 | 3.4 |
| | | 1.0 | 0.1 | 379 | 46 | 12.1 |
| | | 2.0 | 0.2 | 251 | 27 | 10.7 |
| | 3.0 | | 0.2 | 227 | 13 | 5.7 |

Figure 3:
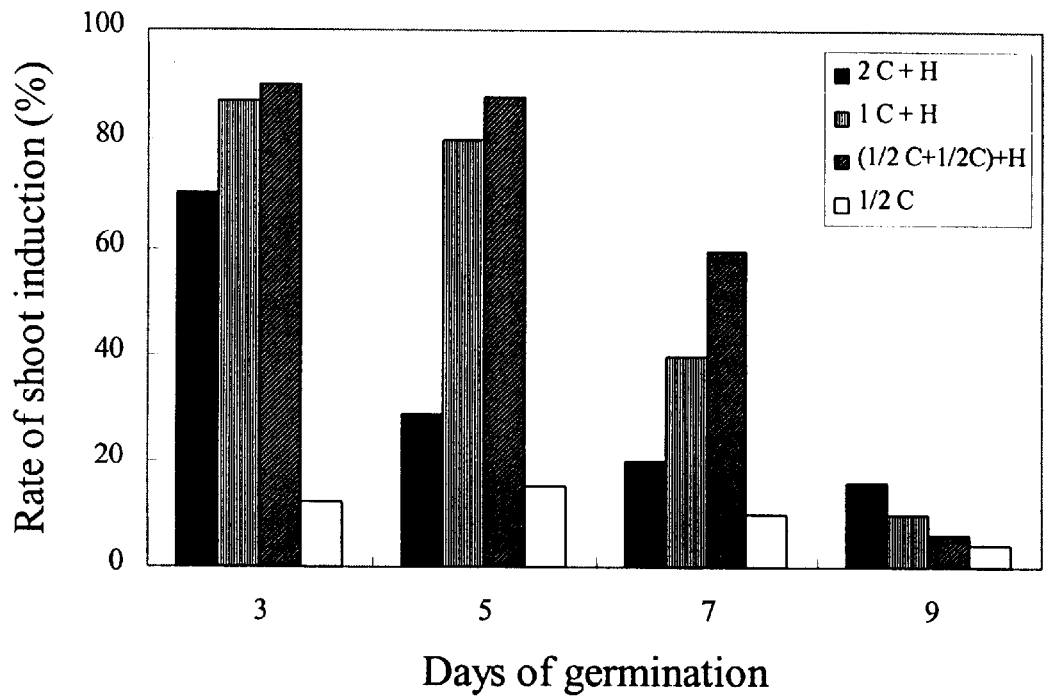
FIG. 3 depicts the relationship between the ages of cucumber seedlings and the frequencies of adventitious shoot induction from various cultured tissues, where.

As shown in Table 1, the prior art method, in which only cotyledon segments are cultured by the same process described in Example 1, has shown at most 20% of induction efficiency (see also FIG. 3).

Example 3
Comparative plant regeneration from cucumber hypocotyl segments by somatic embryogenesis In this Example, cucumber seeds were germinated by the same process as described in Example 2, except for being germinated in a dark room. The 5~10 mm-length hypocotyls of 5 DAG seedlings were excised and cultured on callus induction media [MS media (pH 5.8) supplemented with 3, 5, or 10% sucrose, 0.4% Phytagel, and 1.0 mg/L 2,4- dichlorophenoxy acetic acid (2,4-D)]. Embryogenic calli, which were selected through subcultures on the same media, were maintained and proliferated. In order to induce somatic embryo, the embryogenic callus cultured for 2 weeks on the above media was transferred onto the media without 2,4-D, and further cultured. After 4 weeks, white callus was formed from most of the hypocotyl segments, occasionally pale yellow callus formed. After the pale yellow callus was separated and subcultured, viscous and clear callus was produced on a contact surface to medium, finally forming yellowish embryogenic callus. However, the induction of this embryogenic callus showed poor efficiency, with a callus induction frequency of about 2.5%.

Only 2.3% of hypocotyls formed embryogenic callus in cucumber cultivars Nakhap series (Chosengnakhap and Changhyongnakhap), when the explants were cultured in darkness and under 3% sucrose condition. In other cultivars, no embryogenic callus was induced, even though sucrose was added to the media up to 10% concentration.

Example 4

Adventitious shoot induction from hypocotyl sections of seedlings such as Chinese matrimony vine, red pepper, melon, bean, and spring onion In this Example, regenerated plants were produced from adventitious shoots of various seed plants, by the similar process as described in Example 1. These seed plants include Chinese matrimony vine (*Lycium chinense* Mill) as a member of woody plants, red pepper (*Capsicum annuum* L.) as vegetables, melon (*Cucumis melo* L.) as Cucurbitaceae family, bean (*Phaseolus vulgaris* L.) as legumes, and spring onion (*Allium fistulosum* L.) as monocotyledons. The seeds of the above species were sterilized and germinated as described in Example 1. Each cotyledon was removed by halves or completely from germinated seedlings, and their hypocotyls were excised to 2 mm-length. Excised seedlings were transferred onto the media for adventitious shoot induction, with the hypocotyl section of the seedlings contacting the media.

The excised hypocotyls of Chinese matrimony vine, red pepper, melon, bean and spring onion abundantly produced adventitious shoots in 3 weeks after transfer onto the media (see FIGS. 5a–5e), similar to cucumber. While the adventitious shoots in red pepper, bean and spring onion were successfully induced under the same light conditions as in cucumber, the shoots of Chinese matrimony vine and melon were not. Instead of being cultured under light, excised seedlings of Chinese matrimony vine and melon were cultured for first 2 weeks in darkness, and then transferred to light conditions, so that the adventitious shoots could be frequently induced from these seedlings.

Example 5

Cloning and sequencing cassava SOD gene and constructing expression vector for plant transformation The method for inducing adventitious shoot from hypocotyl section, developed by the above Example, was exploited to produce transgenic cucumber overexpressing SOD. To do this, an expression vector for transforming plants was constructed (see FIG. 1). The expression vector in this Example, employs ascorbate oxidase (ASO) promoter as a promoter, mSOD1 isolated from cassava cultured cells as an SOD structural gene, and the Basta-resistant (bar) gene as a selectable marker.

At first, in order to construct the above vector, an SOD gene was isolated from cassava (*Manihot esculenta*) and sequenced. SOD genes have been isolated from more than 30 species, but we identified a CuZn SOD gene (mSOD1, described in SEQ ID NO. 1) which is the first SOD gene isolated from cassava cultured cells. To isolate a full-length SOD cDNA, we screened a cDNA library which was constructed in Uni-ZAP vector (Stratagene). Particularly, various pools of cassava cultured cells were screened to select those who expressed high level of SOD. The selected cells were subcultured for 20 days, and mRNA was extracted from the cells. After cDNA was synthesized using the isolated mRNA as template, $4 \times 10^5$ pfu (plaque forming unit) of cDNA library was constructed with Gigapack III packaging extract (Stratagene) and the synthesized cDNA, and finally amplified to $2 \times 10^{10}$ pfu/mL. To synthesize probe for screening the cDNA library of cassava cultured cells, two degenerate primers, SODF1 (described in SEQ ID NO. 3) and SODR2 (described in SEQ ID NO. 4), were used, whose nucleotide sequences were deduced from the conserved amino acids sequences among various plant SOD genes. The 312 bp product of PCR, in which SODF1 and SODR2, and the cassava cDNA library were used as primers and template respectively, were inserted into EcoRV site of pBluescript vector (Stratagene), and the resulting vector was introduced into *E. coli*. The plasmid was isolated from the *E. coli*, then cleaved at XbaI and SalI sites. After selection of plasmids releasing 0.5 kb inserts, the selected plasmids were sequenced to prove them to be a partial SOD gene, and thus could be used to screen the cDNA library of cassava cultured cells. The $^{32}$P-dCTP-labeled probe for screening the cDNA library was synthesized from the 0.5 kb PCR product and used to screen $4 \times 10^6$ pfu of the cDNA library twice. As a result, about 50 single plaques were obtained, and 10 selected plaques were sequenced to isolate a full-length CuZn SOD cDNA (mSOD1), which was described in SEQ ID NO. 1.

Isolated mSOD1 was 801 bp cDNA, and had an open reading frame (ORF) comprising 152 amino acid residues. mSOD1 was identified to have a poly-(A) tail and a putative polyadenylation signal, AATAAA sequence, which lay 170 bp upstream from the poly-(A) tail (see SEQ ID NO. 1). When the deduced amino acid sequence from the above ORF (described in SEQ ID NO. 1 and NO. 2) was compared with other plant CuZn SOD sequences, there were 5 conserved amino acid sequences (MVKAEAVL, PGLHGFHVH, GDTTNGC, DDLGRGGHELS, TGNAGGR), and putative copper-binding sites (His-45, His-47, His-62, His-70, His-79, Asp-82 and His-119).

ASO promoter was inserted to pBluescript vector (Stratagene) at first, in order to construct the expression vector for transforming plants which comprised the isolated mSOD1, the fruit-dominant ASO promoter of cucumber, and Basta-resistant (bar) gene. Particularly, the sequence of ASO promoter (distributed by Nara Institute of Science and Technology in Japan; *Ann. N. Y. Acad. Sci.* 721, 245–247) was amplified by PCR in which two PCR primers (described in SEQ ID NO. 5 and 6, respectively) were tagged with HindIII or EcoRI restriction sequences, respectively, at their 5' ends. This PCR product was cleaved by HindIII and EcoRI restriction enzymes, and inserted into HindIII/EcoRI site of pBluescript KS vector, to produce vector ASOp/pBluescript.

To insert the isolated mSOD1 into ASOp/pBluescript, the PstI- or BamHI-tagged primers (described in SEQ ID NO. 7 and 8, respectively) and template of the full-length mSOD1 cDNA were used to obtain PCR product for mSOD1, which was then inserted into PstI/BamHI site of the vector ASOp/pBluescript. The resulting vector was designated as ASOp+mSOD1 /pBluescript.

To insert ASOp+mSOD1 fragment of ASOp+mSOD1/pBluescript into pBI101 (Clontech), a binary vector for transforming plants, the vector ASOp+mSOD1/pBluescript was digested with HindIII and BamHI enzymes, and pBI101 with HindIII and SacI enzymes. After BamHI site and SacI site were made to be blunt ends, the ASOp+mSOD1 fragment was inserted into HindIII/SacI site of pBI101. The resulting vector was designated as ASOp+mSOD1/pBI101.

Finally, vector pGPTV-Bar Plant Mol. Biol. 20, 1195–1197, 1992; ATCC Accession NO. 77391) was employed so that bar gene in pGPTV-Bar might replace the selection marker in pBI101. Particularly, the vector ASOp+ mSOD1/pBI101 was digested with HindIII enzyme and partially digested with EcoRI enzyme, producing about 2 kb fragment. This fragment was inserted into HindIII/EcoRI site of pGPTV-Bar, constructing vector ASOp+mSOD1/ pGPTV-Bar (see FIG. 1).

To introduce the vector ASOp+mSOD1/pGPTV-Bar into *Agrobacterium tumefaciens* LBA 4404 strain, the vector was mixed with *Agrobacterium tumefaciens* LBA 4404. The mixture was frozen in liquid nitrogen for 5 minutes, and thawed at 37° C. for 5 minutes. After 1 mL of YEP solution (1% bacto-peptone, 1% bacto-yeast extract, 0.5% sodium chloride) was added to the mixture, Agrobacterium in the mixture was cultured at 28° C. with shaking and then spread on YEP medium (YEP solidified by 1.5% bacto-agar) containing 50 mg/L kanamycin and 100 mg/L rifampicin. The medium was cultured at 28° C. for 2 days to isolate the colonies of Agrobacterium transformants. The transformed strain was isolated, designated as *Agrobacterium tumefaciens* LBA 4404 (ASOp+mSOD1/pGPTV-Bar), and deposited in Korean Collection for Type Cultures (KCTC) on Mar. 6, 1999 (KCTC Accession NO. 0585BP).

Example 6
SOD gene transfer into cucumber hypocotyl sections and the production of transgenic cucumbers The method in the present invention for inducing adventitious shoot is applicable to efficient production of plants into which a useful gene is introduced. In this Example, hypocotyl sections of cucumber seedlings were infected with the strain *Agrobacterium tumefaciens* LBA 4404 (ASOp+mSOD1/pGPTV-Bar), which mediated the transfer of vector ASOp+mSOD1/pGPTV-Bar into cucumber. At first, cucumber seeds were germinated on MS media in a sterile condition as described in Example 1. After the upper hypocotyls of the germinated seedlings were excised to discard lower parts, the hypocotyl sections were infected with *Agrobacterium tumefaciens* LBA 4404 (ASOp+ mSOD1/pGPTV-Bar) which had been cultured for 2 days in YEP solution containing 50 mg/L kanamycin and 100 mg/L rifampicin. After draining off the soaked hypocotyl region, the seedlings were transferred to the media for adventitious shoot induction (the MS media supplemented with 2.0 mg/L zeatin), with the hypocotyl section contacting the media. The seedlings on the media were cultured for 4 days, with a photoperiod of 16 hours under fluorescent light (intensity: about 15 $\mu$mol m$^{-2}\cdot$s$^{-1}$) and 8 hours under darkness, so as to infect hypocotyl section with the Agrobacterium. To remove Agrobacterium and to select transformed adventitious shoots, the seedlings were transferred onto selective medium (an MS medium supplemented with 2.0 mg/L zeatin, 300 mg/L claforan and 2.0 mg/L Basta). By subculturing the seedlings every week, Basta-resistant adventitious shoots were induced from the hypocotyl sections of the seedlings in 4 weeks after transfer (see FIG. 6a). After leaves developed from the adventitious shoots, the selected shoots were transferred to media for root induction, the MS media supplemented with 1.0 mg/L IAA (see FIG. 6b). The resulting transformants were transferred and acclimatized to pots in a greenhouse (see FIG. 6c).

To inquire whether or not bar gene is stably introduced to the genome of Basta-resistant plantlets, PCR was performed, in which two oligonucleotides (described in SEQ ID NO. 9 and 10) designed from bar gene were used as primers. 10 plantlets with 3–4 leaves were randomly selected, and then their leaves were ground to obtain genomic DNA, which was employed as a template in the PCR. As a result, it was revealed that PCR products from about 60% of Basta-resistant plantlets contained 0.5 kb DNA of bar gene (see FIG. 7).

In this Example, it was confirmed that the SOD transgenic cucumber could be well developed, by using the novel method of inducing adventitious shoot and using fruit-dominant promoter in cucumber.

Industrial Applicability

As described above, transgenic plants, and more specifically, the fruits of transgenic cucumber, showing far higher SOD activity than existing cultivars do, is produced in the present invention through the method in which an expression vector for plant transformation, comprising a cucumber fruit-dominant promoter (ASO promoter), an SOD gene (mSOD1) and a herbicide-resistant gene (bar), is introduced into Agrobacterium, the resulting Agrobacterium transformant mediates the SOD gene transfer into hypocotyl sections, and tranformed adventitious shoot is induced from the hypocotyl sections to be regenerated. Such SOD transgenic cucumber not only can be used as materials of cosmetics including massage packs, additives in functional foods, medicines and so on, but also is tolerant to herbicides and various environmental stresses.

In addition, the method for inducing adventitious shoot in the present invention is applicable to propagating useful plants or regenerating transformed tissues to adult plants more faithfully and less laboriously than the established methods. Therefore, the tissues of plants recalcitrant against adventitious shoot induction or the induction of somatic embryos can be regenerated and propagated repeatedly through the method of the present invention, which can be used for the propagation of useful plants and the development of useful transgenic plants.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for producing a transgenic Cucurbitaceae plant comprising:
   (a) constructing an expression vector for plant transformation that comprises a cucumber fruit-dominant promoter, a superoxide dismutase (SOD) gene derived from cassava, and a selectable marker gene;
   (b) transferring the vector constructed in step (a) to a transformant;
   (c) co-culturing the transformant of step (b) with Cucurbitaceae plant tissue; and
   (d) regenerating the transformed tissue into a mature transgenic plant.

2. The method of claim 1, wherein the Cucurbitaceae plant tissue is selected from the group consisting of cucumber (*Cucumis sativus* L.), pumpkin (*Cucurbita* spp.), watermelon (*Citrullus vulgaris*), and melon (*Cucumis melo* L.).

3. The method of claim 1, wherein the cucumber fruit-dominant promoter is an ascorbate oxidase (ASO) promoter.

4. The method of claim 1, wherein the SOD gene comprises the nucleotide sequence shown in SEQ ID NO:1.

Figure 1:
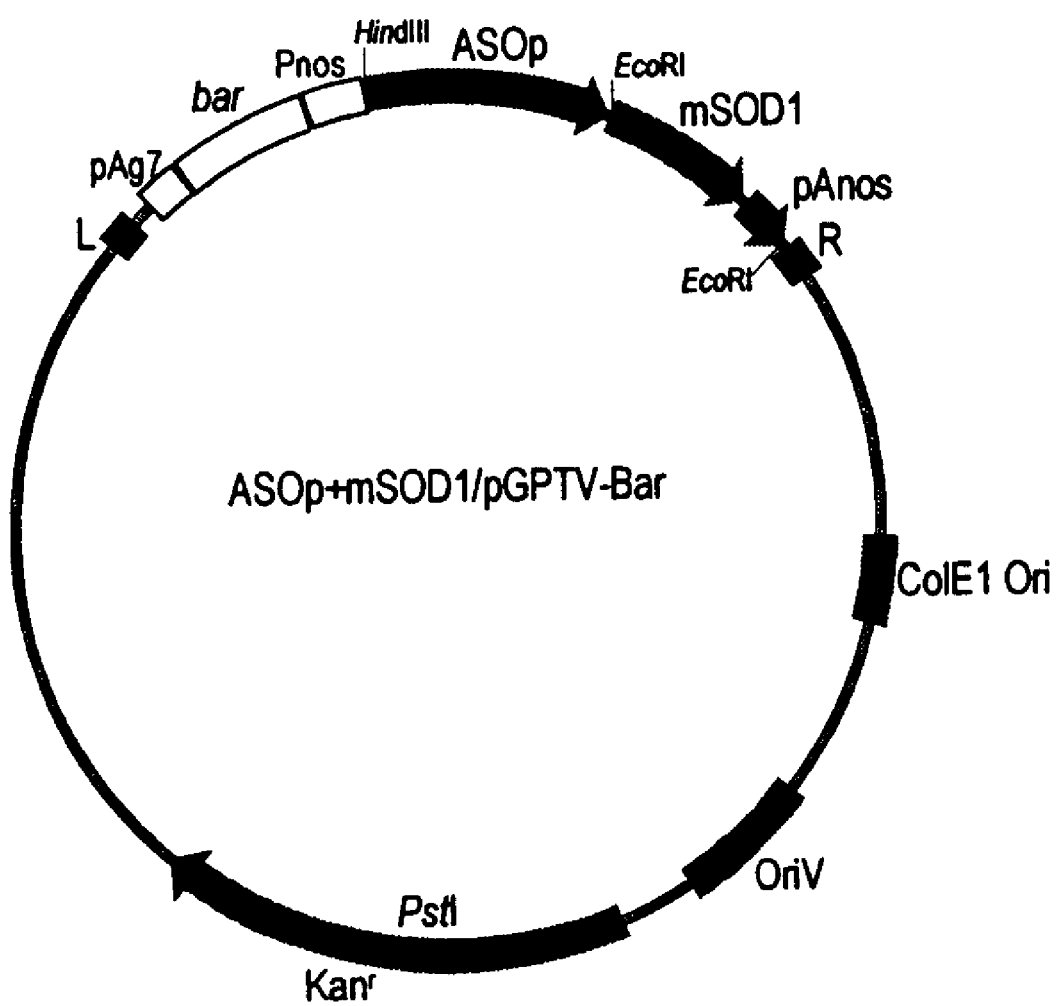
FIG. 1 depicts a vector system of the present invention.

5. The method of claim 1, wherein the expression vector has a restriction map as shown in FIG. 1 and designated ASOp+mSOD1/pGPTV-Bar.

6. The method of claim 1, wherein the selectable marker gene comprises an herbicide-resistant gene.

7. The method of claim 6, wherein the herbicide-resistant gene comprises a bar gene.

8. The method of claim 1, wherein the transformant is *Agrobacterium tumefaciens*.

9. The method of claim 8, wherein the *Agrobacterium tumefaciens* is *Agrobacterium tumefaciens* LBA 4404 having KCTC Accession No. 0585BP.

10. The method of claim 1, wherein the co-culturing of step (c) comprises:
   (i) excising hypocotyl segments bearing cotyledons of a germinated seedling to eliminate the root portion of the seedling;
   (ii) infecting the excised hypocotyl segments bearing cotyledons with the transformant of step (b); and
   (iii) culturing the infected hypocotyl segments bearing cotyledons in medium under conditions sufficient for adventitious shoot induction.

11. The method of claim 10, wherein the regenerating of step (d) comprises:
   (i) inducing adventitious shoot from the infected hypocotyl segments bearing cotyledons in selective medium;
   (ii) rooting the induced adventitious shoot in medium under conditions sufficient for root induction; and
   (iii) acclimatizing the rooted plantlet to soil.

12. The method of claim 10, wherein the excised hypocotyl segments bearing cotyledons are approximately 2 to approximately 3 mm in length.

13. The method of claim 10, wherein the hypocotyl segments bearing cotyledons are excised at about 3 to about 5 days after germination.

14. The method of claim 10, wherein the hypocotyl segments bearing cotyledons are excised at about 3 to about 5 days after the germinated seedling has one intact cotyledon or two half-cotyledons.

15. A transgenic Cucurbitaceae plant produced by the method of claim 1.

16. A composition comprising a transgenic Cucurbitaceae plant of claim 15 or a derivative thereof, and a carrier.

17. The composition of claim 16 which is a cosmetic composition, a nutriceutical composition or a pharmaceutical composition.

* * * * *